(12) United States Patent
Alva et al.

(10) Patent No.: US 7,989,631 B2
(45) Date of Patent: Aug. 2, 2011

(54) HYDRATE FORMS OF AMG706

(75) Inventors: Gonzalo Alva, Moorpark, CA (US); Seshadri Neervannan, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1148 days.

(21) Appl. No.: 11/627,803

(22) Filed: Jan. 26, 2007

(65) Prior Publication Data

US 2008/0039501 A1    Feb. 14, 2008

Related U.S. Application Data

(60) Provisional application No. 60/772,397, filed on Feb. 10, 2006.

(51) Int. Cl.
*C07D 401/14* (2006.01)
(52) U.S. Cl. .................................... 546/256
(58) Field of Classification Search .................. 546/256; 514/333
See application file for complete search history.

(56) References Cited

U.S. PATENT DOCUMENTS

| | | | |
|---|---|---|---|
| 5,990,141 A | 11/1999 | Hirth et al. | |
| 6,001,961 A | 12/1999 | Jonczyk et al. | |
| 6,235,764 B1 | 5/2001 | Larson et al. | |
| 6,258,812 B1 | 7/2001 | Bold et al. | |
| 6,627,646 B2 * | 9/2003 | Bakale et al. | 514/322 |
| 6,878,714 B2 | 4/2005 | Askew et al. | |
| 6,995,162 B2 | 2/2006 | Chen et al. | |

FOREIGN PATENT DOCUMENTS

| | | |
|---|---|---|
| EP | 0 407 122 A1 | 1/1991 |
| EP | 0 970 070 B1 | 10/2004 |
| JP | 02233610 | 9/1990 |
| WO | 99/45009 A1 | 9/1999 |
| WO | 99/61422 A1 | 12/1999 |
| WO | 00/02871 A1 | 1/2000 |
| WO | 00/12089 A1 | 3/2000 |
| WO | 00/59509 A1 | 10/2000 |
| WO | 01/32651 A1 | 5/2001 |
| WO | 01/37820 A2 | 5/2001 |
| WO | 02/055501 A2 | 7/2002 |
| WO | 02/059110 A1 | 8/2002 |
| WO | 02/066470 A1 | 8/2002 |
| WO | 02/068406 A3 | 9/2002 |
| WO | 2004/005279 A3 | 1/2004 |
| WO | 2004/007458 A1 | 1/2004 |
| WO | 2004/007481 A3 | 1/2004 |
| WO | 2004/009784 A3 | 1/2004 |

OTHER PUBLICATIONS

Chemical & Engineering News, Feb. 2003, 32-35.*
Brittain et al., "Polymorphism in Pharmaceutical, etc.," "NY: Marcel Dekker, Inc., 1999, 1-2, 125-181,183-226.*
US Pharmacopia #23, National Formulary #18 (1995), 1843-1844.*
Vippagunta et al., "Crystalline Solids", Advanced Drug Delivery Reviews 48 (2001) 3-26.*
Doelker, "Physiochemical behavior, etc.," S.T.P. Pharma Pratiques (1999), 9(5), 399-409 and english translation pp. 1-39.*
CMU Pharmaceutical polymorphism, intenet p. 1-3 (2002) (printout Apr. 3, 2008).*
Singhal et al., "Drug polymorphism, etc.," "Advanced drug delivery reviews 56, 335-347 (2004).*
Caira, "Crystalline Polymorphism of Organic Compounds", Topics in Current Chemistry, 198, Berlin Heidlberg: Spring Verlag 1998, 184-208.*
Muzaffar et al., Polymorphism and Drug Availability, etc., J of Pharm. (Lahore), 1979, 1(1), 59-66.*
Jain et al., "Polymorphism in Pharmacy", Indian Drugs, 1986, 23(6), 315-329.*
Taday et al., "Using Terahertz, etc.," J. of Pharm. Sci.., 92(4), 2003, 831-838.*
Otsuka et al., "Effect of Polymorphis Forms, etc.," Chem. Pharm. Bull. 47(6) 852-856 (1999).*
Ovid Copyright #2013210, "R & D Focus", Drug Name, Motesanib, (2004).
Bush, et al., "Anti-tumor Activity of Motesanib Diphosphate Alone and in Combination with Docetaxel or Tamoxifen in Xenograft Models of Human Breast Carcinome", Breast Can. Res. And Treatment, 106(1):S77 (2007).
Milano, et al., "New Molecular Targeted Therapies in Thyroid Cancer", Anti-Cancer Drugs, 17(8):869-879 (2006).
Polverino, et al., "AMG 706, an Oral Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Can. Res., 66(77):8715-8721 (2006).
Rosen, et al., "Safety, Pharmacokinetics, and Efficacy of AMG 706, an Oral Multikinase Inhibitor, in Patients with Advanced Solid Tumors", J. of Clin. Oncology, 25)17): 2369-2376 (2007).
Sherman, et al., "Motesanib Diphosphate in Progressive Differentiated Thyroid Cancer", New England J. of Medicine, 359(1):31-42 (2008).
Sorbera, et al., Oncolytic Antiangiogenic Agent Multikinase Inhibitor, Drugs of the Future, 31(10):847-853 (2006).
Wadke, et al., "Pharmaceutical Dosage Forms", 2nd Edition, ed. Herbert A. Lieberman, Published by Marcel Dekker, New York, 1:34-36 (1989).
Ovid Copyright #11016, "R & D Insight", Drug Name, Motesanib, (2003).
Ovid Copyright #037998, "Pharmaprojects", Drug Name, Motesanib Diphosphate, (2007).

* cited by examiner

*Primary Examiner* — Patricia L Morris
(74) *Attorney, Agent, or Firm* — Joseph W. Bulock

(57) ABSTRACT

The anti-angiogenic drug AMG 706 is provided in the monophosphate hydrate form. Also provided is AMG 706 drug substance wherein the AMG 706 is present, in at least a detectable amount, as AMG 706 phosphate dihydrate. Also provided are processes for preparing AMG 706 phosphate dihydrate, AMG 706 drug substance of the invention, and a pharmaceutical composition of the invention. Also provided is a method of treating a medical condition or disorder in a subject where treatment with an anti-angiogenic is indicated, comprising administering, for example orally, a composition of the invention in a therapeutically effective amount.

9 Claims, 2 Drawing Sheets

Figure 1: Representative DSC of AMG 706 - Monophosphate Dihydrate
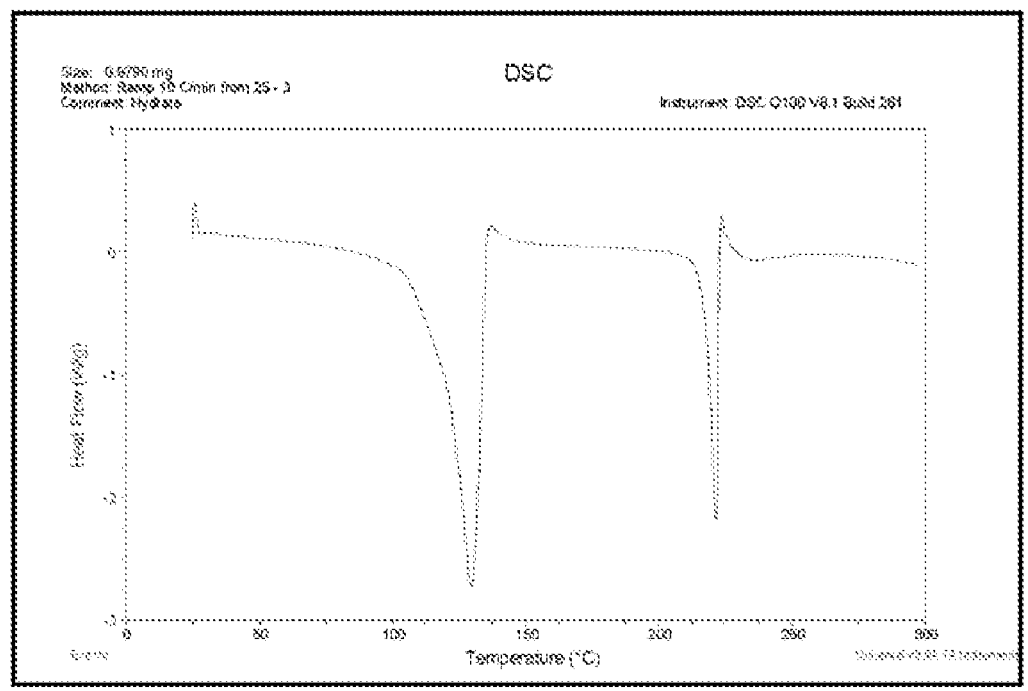
Figure 2. DSC of AMG 706-diphosphate, Instrument: Q100
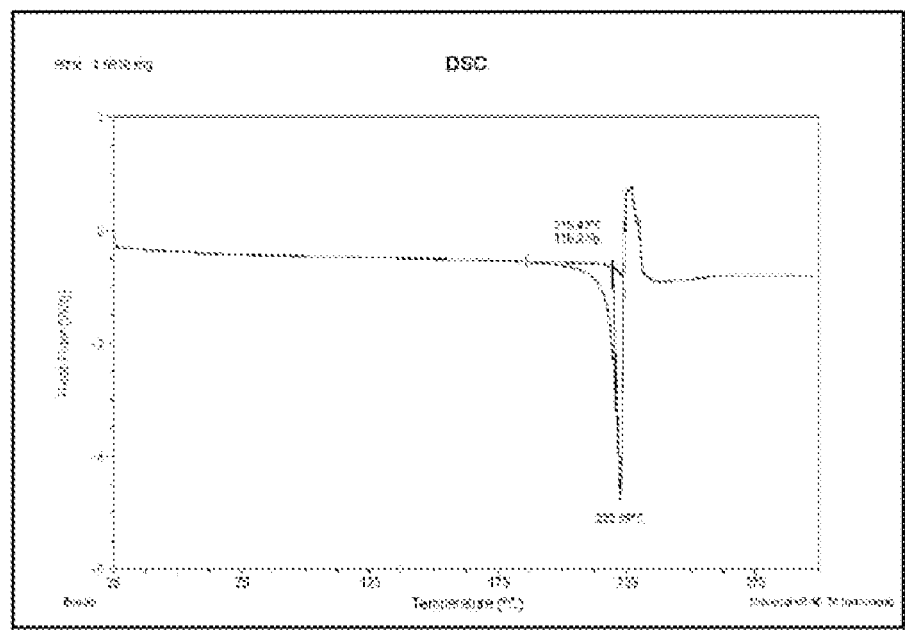

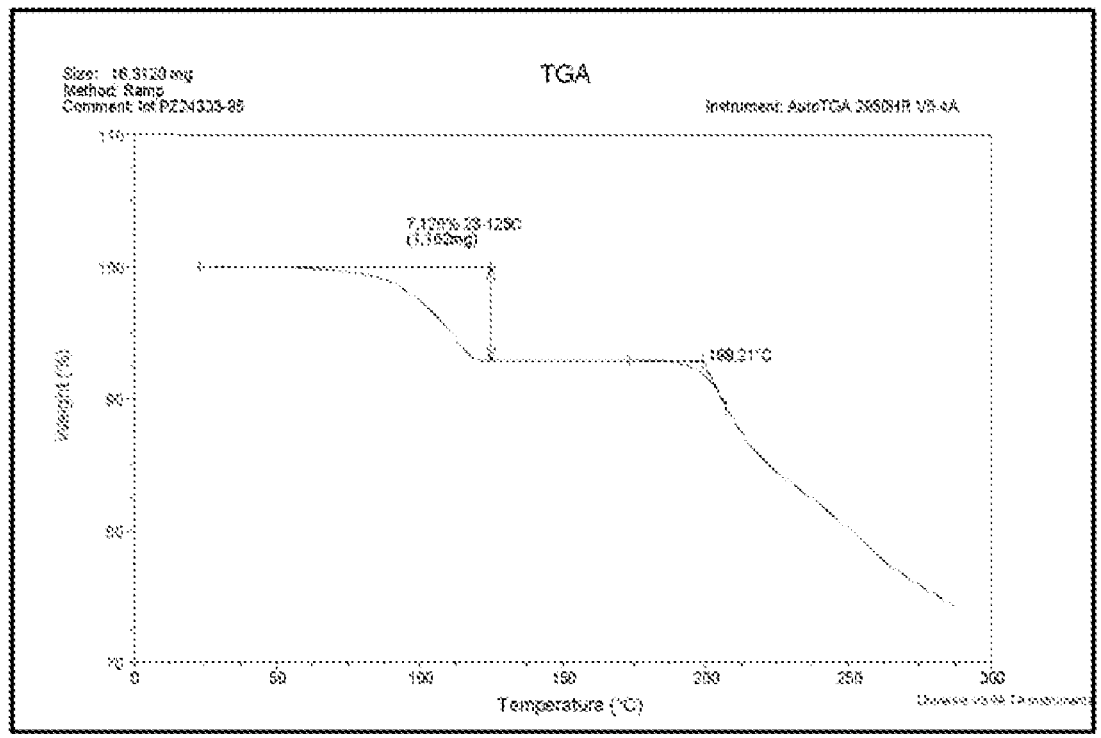
Figure 3: Representative TGA of AMG 706-02 - Monophosphate Dihydrate

HYDRATE FORMS OF AMG706

This application claims the benefit of U.S. Provisional Application No. 60/772,397 Feb. 10, 2006, which is hereby incorporated by reference.

FIELD OF THE INVENTION

The present invention relates to hydrate phosphate salt forms of AMG 706, to pharmaceutical compositions comprising such solid-state forms, and to processes for preparing them. The invention further relates to methods of treatment of angiogenesis mediated disorders comprising administering such solid-state forms or compositions thereof to a subject, and to use of such solid-state forms in the manufacture of medicaments.

BACKGROUND OF THE INVENTION

AMG 706, also known as motesanib or N-(2,3-dihydro-3,3-dimethyl-1H-indol-6-yl)-2-[(4-pyridinylmethyl)amino]-3-pyridinecarboxamide, and its pharmaceutically acceptable salts including the diphosphate salt, has a therapeutic and prophylactic anti-angiogenic effect. AMG 706 has utility in treatment and prevention of angiogenesis-mediated disorders, including the treatment of cancer.

BRIEF DESCRIPTION OF THE DRAWINGS

FIG. 1 shows a differential scanning calorimetry (DSC) thermogram of the dihydrate phosphate salt form of AMG 706 drug substance.

FIG. 2 shows a differential scanning calorimetry (DSC) thermogram of the anhydrous diphosphate salt form of AMG 706 drug substance.

FIG. 3 shows a thermogravimetric analysis (TGA) profile of the dihydrate phosphate salt form of AMG 706 drug substance.

DETAILED DESCRIPTION OF THE INVENTION

U.S. Pat. Nos. 6,995,162 and 6,878,714 describe a family nicotinamides, including AMG706, and pharmaceutically acceptable salts thereof, as anti-angiogenic agents.

A preferred salt form of AMG 706 is the diphosphate salt. A need exists for new forms of AMG 706, in particular thermodynamically stable forms suitable for preparing pharmaceutical compositions, including aqueous suspensions.

As indicated hereinbelow, treatment with AMG 706 is indicated in a very wide array of angiogenesis-mediated conditions and other disorders. Therefore, in the use of the thermodynamically stable hydrate monophosphate salt form, especially the dihydrate form, a significant advance would be realized in treatment of angiogenesis mediated conditions and disorders.

The anhydrous diphosphate sale of AMG 706 is currently manufactured as a crystalline form. This crystalline form is used in the table formulations for clinical trials. We have found that the anhydrous diphosphate salt can disproportionate and convert to a more stable monophosphate hydrate salt in the presence of water or aqueous co-solvent mixtures.

Accordingly, the present invention provides a hydrate phosphate salt form of AMG 706. There is also provided AMG 706 drug substance wherein the AMG 706 is present, in at least a detectable amount, as hydrate phosphate salt form of AMG706. The term "AMG 706 drug substance" as used herein means AMG 706 per se as qualified by the context in which the term is used, including a detectable amount of the hydrate monophosphate salt form and can refer to unformulated AMG 706 or to AMG 706 present as an ingredient of a pharmaceutical composition.

Also provided are processes for preparing a hydrate phosphate salt form of AMG 706, and for preparing the AMG 706 hydrate phosphate drug substance of the invention. AMG 706 hydrate phosphate drug substance or powder thereof, prepared according to such processes can be further formulated to provide a pharmaceutical dosage form. Preferably the hydrate is the AMG 706 dihydrate phosphate salt form.

Also provided is a method of treating a medical condition or disorder in a subject where treatment with an angiogenesis inhibitor is indicated, comprising administering, for example orally, a composition of the invention in a therapeutically effective amount. Such method is particularly useful where the medical condition or disorder is angiogenesis.

The invention provides novel hydrate phosphate salt forms of AMG 706, preferably the dihydrate form. In addition to hydrate phosphate salt form of AMG 706 per se, the invention provides AMG 706 drug substance that comprises the hydrate phosphate salt form of AMG 706. At least a detectable amount of the hydrate phosphate salt form of AMG 706 is present. Preferably, about 10% to about 100%, more preferably about 25% to about 100%, still more preferably about 60% to about 100%, and even more preferably about 80% to about 100%, by weight of the AMG 706 in an AMG 706 drug substance of the invention is the hydrate phosphate salt form, preferably the dihydrate phosphate salt form. In a particular embodiment, substantially all of the AMG 706 is hydrate phosphate salt form, i.e., the AMG 706 drug substance is substantially pure hydrate phosphate salt form of AMG 706.

In one embodiment, the amount of hydrate phosphate salt form of AMG 706 in an AMG 706 drug substance is sufficient to provide an anti-angiogenic effect, wherein all, or a substantial portion of, the AMG 706 is substantially hydrate salt form, preferably the dihydrate phosphate salt form.

The hydrate phosphate salt form of AMG 706 or AMG 706 drug substance of the invention can be prepared by any suitable process, not limited to processes described herein. AMG706 can be added to an aqueous solution, including alcoholic solutions, e.g. solutions with ethanol. For example solutions can be used with less than about 25% ethanol. Preferably the AMG706 is dissolved in the aqueous solution. The aqueous solution is preferably heated to a temperature above room temperature, such as above about 50° C., preferably at boiling. Hydrate material in a solid form can be collected upon cooling. Preferably the cooling occurs over three hours.

AMG 706 drug substance or drug powder prepared according to the above process or any other process can be administered orally, rectally or parenterally without further formulation, or in simple suspension in water or another pharmaceutically acceptable liquid. Alternatively, the AMG 706 drug substance or drug powder can be directly filled into capsules for oral administration. Preferably, however, AMG 706 drug substance or drug powder is subjected to further processing, typically with one or more excipients, to prepare a pharmaceutical composition, for example an oral dosage form, as described herein below.

The hydrate phosphate salt form of AMG 706, or AMG 706 drug substance as provided herein can be further formulated together with one or more pharmaceutically acceptable excipients to produce a pharmaceutical composition. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a capsule or table suitable for oral administration. Excipients include, by way of illustration and not limitation, diluents, disintegrants, binding agents, adhesives, wetting agents, lubricants, glidants, crystallization inhibitors, surface-modifying agents, substances added to mask or counteract a disagreeable taste or odor, flavors, dyes, fragrances, and substances added to improve appearance of the composition.

Excipients employed in compositions of the invention can be solids, semi-solids, liquids or combinations thereof. Compositions of the invention containing excipients can be prepared by any known technique of pharmacy that comprises admixing an excipient with a drug or therapeutic agent. A composition of the invention contains a desired amount of AMG 706 hydrate per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended for parenteral administration, it can be in the form, for example, of a suspension. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention. Compositions of the invention optionally comprise one or more pharmaceutically acceptable diluents as excipients. Suitable diluents illustratively include, either individually or in combination, lactose, including anhydrous lactose and lactose monohydrate: starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents: confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; poly vinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility. Lactose and microcrystalline cellulose, either individually or in combination, are preferred diluents. Both diluents are chemically compatible with AMG 706 hydrate. The use of extragranular microcrystalline cellulose (that is, microcrystalline cellulose added to a wet granulated composition after a drying step) can be used to improve hardness (for tablets) and/or disintegration time. Lactose, especially lactose monohydrate, is particularly preferred. Lactose typically provides compositions having suitable release rates of AMG 706, stability, pre-compression flowability, and/or drying properties at a relatively low diluent cost. It provides a high density substrate that aids densification during granulation (where wet granulation is employed) and therefore improves blend flow properties.

Suspensions can be prepared similar to that described in Formulation technology: emulsions, suspensions, solid forms; Hans Mollet and Arnold Grubenmann; Pharmaceutical Emulsions and Suspensions; Fransiose Nielloud, CRC: 1st ed. (2000), or Pharmaceutical Dosage Forms: Disperse Systems, Vol 1 and Vol 2, Ed.: Herbert Lieberman, Martin Rieger, Gilbert Banker, Marcel Dekker, N.Y.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colorcon™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums. Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition. Croscarmellose sodium is a preferred disintegrant for tablet or capsule disintegration, and, if present, preferably constitutes about 0.2% to about 10% more preferably about 0.2% to about 7%, and still more preferably about 0.2% to about 5%, of the total weight of the composition. Croscarmellose sodium confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1551 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the AMG 706 hydrate in close association with water, a condition that is believed to improve bioavailability of the composition. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatting acid esters, for example propylene glycol laurate (e.g., Lauroglycol™ of Gatterfossé), sodium lauryl sulfate, fatty acids and salts thereof, for example oleic acid, sodium oleate and triethanolamine oleate, glyceryl fatty acid esters, for example glycerylmonostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10% and more preferably about 0.5% to about 5%, of the total weight of the composition. Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including antiadherents and/or glidants) as excipients. Suitable lubricants include, either individually or in combination, glycerylbehapate (e.g., Compritol™ 888); stearic acid and salts thereof, including magnesium, calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition. Magnesium stearate is a preferred lubricant used, for example, to reduce friction between the equipment and granulated mixture during compression of tablet formulations.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred. Other excipients such a colorants, flavors and sweeteners are known in the pharmaceutical art and can be used in compositions of the present invention. Tablets can be coated, for example with an enteric coating, or uncoated. Compositions of the invention can further comprise, for example, buffering agents. Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70% for example about 60%, by weight of the composition.

An effervescent agent, present in a solid dosage form in an amount less than that effective to promote disintegration of the dosage form, provides improved dispersion of the AMG 706 hydrate in an aqueous medium. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the composition. An "effervescent agent" herein is an agent comprising one or more compounds which, acting together or individually, evolve a gas on contact with water. The gas envolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid. Non-limiting examples of suitable buses as components of effervescent agents useful in the invention include carbonate salts (e.g., calcium carbonate), bicarbonate salts (e.g., sodium bicarbonate) sesquicarboante salts, and mixtures thereof. Calcium carbonate is a preferred base. Non-limiting examples of suitable acids as components of effervescent agents useful in the invention include citric acid, tartaric acid, malic acid, faimaric acid, adipic acid, succinic acid, acid anhydrides of such acids, acid salts of such acids, and mixtures thereof. Citric acid is a preferred acid. In a preferred embodiment of the invention, where the effervescent agent comprises an acid and a base, the weight ratio of the acid to the case is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Solid dosage forms of the invention can be prepared by any suitable process, not limited to processes described herein. An illustrative process comprises (a) a step of blending hydrate phosphate salt form of AMG 706, or AMG 706 dihydrate drug substance, of the invention with one or more excipients to form a blend, and (b) a step of tableting or encapsulating the blend to form tablets or capsules respectively. In a preferred process, solid dosage forms are prepared by a process comprising (a) a step of blending a hydrate phosphate salt form of AMG 706, or AMG 706 dihydrate drug substance, of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known the art, but is preferably a wet granulation step followed by s step of drying the resulting granulate prior to tableting or encapsulating. One or more diluents, one or more disintegrants and one or more binding agents are preferably added, for example in the blending step, a wetting agent can optionally be added, for example, for example in the blending step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient case so that weight variation can be reliably controlled during capsule filling or tableting, and that is dense enough in bulk so that a catch can be processed in the selected equipment and individual doses fit into the specified capsules or tablet dies.

Conventional tableting and encapsulation techniques known in the art can be employed. Where coated tablets are desired, conventional coating techniques are suitable. Any tablet hardness convenient with respect to handling, manufacture, storage and ingestion can be employed. The material to be tableted, however, should not be compressed to such a degree that there is subsequent difficulty in achieving hydration when exposed to gastric fluid.

AMG 706 hydrate dosage forms of the invention preferably comprise AMG 706 hydrate in a daily dosage amount of about 0.1 mg to about 500 mg, more preferably about 1 mg to about 250 mg, and most preferably about 10 mg to about 175 mg. Compositions of the invention comprise one or more orally deliverable dose units. Each dose unit comprises AMG 706 hydrate in a therapeutically effective amount that is preferably about 10 mg to about 500 mg. The term "dose unit" herein means a portion of a pharmaceutical composition that contains an amount of a therapeutic or prophylctic agent, in the present case AMG 706 hydrate, suitable for a single oral administration to provide a therapeutic effect. Typically one dose unit, or a small plurality (up to about 4) of dose units, in a single administration provides a dose comprising a sufficient amount of the agent to result in the desired effect. Administration of such doses can be repeated as required, typically at a dosage frequency of 1 to about 4 times per day. It will be understood that a therapeutically effective amount of AMG 706 hydrate for a subject is dependent inter alia on the body weight of the subject. A "subject" herein to which a therapeutic agent or composition thereof can be administered includes a human patient of either sex and of any age, and also includes any nonhuman animal, particularly a warm-blooded animal, more particularly a domestic or companion animal, illustratively a cat, dog or horse. When the subject is a child or a small animal (e.g., a dog), for example, an amount of AMG 706 hydrate relatively low in the preferred range of about 10 mg to about 500 mg is likely to provide blood serum concentrations consistent with therapeutic effectiveness. Where the subject is an adult human or a large animal (e.g., a horse), achievement of such blood serum concentrations of AMG 706 are likely to require dose units containing a relatively greater amount of AMG 706 hydrate. Typical dose units in a composition of the invention contain about 10, 20, 25, 37.5, 50, 75, 100, 125, 150, 175, 200, 250, 300, 350 or 400 mg of AMG 706 hydrate. For an adult human, a therapeutically effective amount of AMG 706 hydrate per dose unit in a composition of the present invention is typically about 50 mg to about 400 mg. Especially preferred amounts of AMG 706 hydrate per dose unit are about 100 mg to about 200 mg, for example about 100 mg or about 125 mg. A hose unit containing a particular amount of AMG 706 hydrate can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely. The term "oral administration" herein includes any form of delivery of a therapeutic agent or a composition thereof to a subject wherein the agent or composition is placed in the mouth of the subject, whether or not the agent or composition is immediately swallowed. Thus "oral administration" includes buccal and sublingual as well as esophageal administration. Absorption of the agent can occur in any part or parts of the gastrointestinal tract including the mouth, esophagus, stomach, duodenum, ileum and colon. The term "orally deliverable" herein means suitable for oral administration.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone: and disorders of the female reproductive system such as endometrosis. Such compositions are useful in prevention and treatment of benign and malignant tumors and neoplasia including cancer, such as colorectal cancer, brain cancer, bone cancer epithelial cell-derived neoplasia (epithelial carcinoma) such as basal cell carcinoma, adenocarcinoma, gastrointestinal cancer such as lip cancer, mouth cancer, thyroid cancer, esophageal cancer, small bowel cancer, stomach cancer, GIST, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, GIST, Barrett's esophagus, liver cancer, bladder cancer, pancreatic cancer, ovarian cancer, prostate cancer, thyroid cancer, cervical cancer, lung cancer, breast cancer and skin caner. Besides being useful for human treatment, compositions of the invention are useful for veterinary treatment of companion animals, exotic animals, farm animals, and the like, particularly mammals. More particularly, compositions of the invention are useful for treatment of angiogenesis mediated disorders in horses, dogs and cats.

The terms "treating,""treatment," and "therapy" as used herein refer to curative therapy, adjuvant therapy, prophilactic therapy, and preventative therapy. The term "comprising" is meant to be open ended, including the indicated component but not excluding other elements. The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The present invention is further directed to a therapeutic method of treating a condition or disorder where treatment with an anti-angiogenic drug is indicated, the method comprising oral administration of a composition of the invention to a subject in need thereof. The dosage regimen to prevent, give relief form, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and an therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and closing schedule can be rationally modified over the course of therapy so that the lowest amount of the composition exhibiting satisfactory effectiveness is administered, and so that administration is continued only for so long as is necessary to successfully treat the condition or disorder.

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and other pharmaceutical agent, is intended to embrace administration of each agent in a sequential manner in a regimen that will provide beneficial effects of the drug combination, and is intended as well to embrace co-administration of these agents in substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. AMG 706 hydrate may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commerical use, in clinical evaluation and in pre-clinical development, which would be selected for treatment of neoplasia by combination drug chemotherapy. Such antineoplastic agents fall into several major catergories, namely, antibiotic-type agents, alkylating agents, antimetabolite agents, hormonal agents, immunologicl agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected form but not limited to the group consisting of 5-FU-fibrinogen, acanthifolic acid, aminothiadiazole, brequinar sodium, carmofur, Ciba-Geigy CGP-30694, cyclopentyl cytosine, cytarabinc phosphate stearate, cytarabine conjugates, Lilly DATHF, Merrel Dow DDFC, dexaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable aklylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYK1-17230, hepsul-fam, ifoshamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, Smith Line SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents amy be selected from but not limited to the group consisting of Taiho 4181-A, aclarubicin, actinomycin D, actinoplanone, Erbamont ADR-456, aeroply sinin derivative, Ajinomoto AN-201-II, Ajinomoto AN-3, Nippon Soda anisomycins, anthroacycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, Smith Kline M-TAG, neoenactin, Nippon Kayaku NK-313, Nippon Kayaku NKT-01, SRI Internation NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, traxine, tricrozarin A, Upjohn U-73975, Kyowa Hakko UCN-10028A, Fujisawa WF-3405, Yoshitomi Y-25024 and zorubicin.

A fourth family of anticoplastic agents which may be used in combination with compounds of the present invention consists of a miscellaneous family of antineoplastic agents, including tubulin interacting agents, ropoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benefluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS malcate, dacarbazine, datelliptinium, didemnin-B, dihaematoprophyrin ether, dihydrolenperone, dinaline, distamycin, Toyo Pharmar DM-341, Toyo Parmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosinc, isoglutamine, isotretinoin, Otsuka JI-36, Ramot K-477, Otsuak K-76COONa, Kureha Chemical K-AM, MECT Corp KI-8110, Americn Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyamine derivatives, methylamilinoacridine, Molecular Genetics MGI-126, minactivin, mitonafide, mitoquidone mopidamol,motretinide, Zenyaku Kogyo MST-16, N-(retinoyl)amino acids, Nisshin Flour Milling N-021, N-acylated-dehydroalanines, nafazairom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, pioxantrone, polyhaematoporphyrin, polypreic acid, Efamol prophyrin, probimane, procarbazine, proglumide, Invitron protease nexin I, Tobishi RA-700, razoxane, Sapporo Beweries RBS, restrictin-P, retelliptine, retinoic acid, Rhone-Poulene RP-49532, Rhone-Poulene RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxurdine, capecitabine, celmoleukin, cetrorelix, cladribine, clotrimazole, cytarabine ocfosfate, DA 3030 (Dong-A), daclizumab, denileukin difitox, deslorelin, dexrazoxane, dilazep, docetaxel, docosanol, doxerclciferol, doxifluridine, doxorubicin, bromocriptine, carmustine, cytarabine, flurorouracil, HIT diclofenac, interferon alfa, daunorubicin, doxorubicin, iretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, fallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladeine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, mectoclopramide, mifepristone, miltefosinc, mirimostim, mismatched double stranded RNA, mitoguazone, mitolactol, mitoxantrone, molgramostim, nafarelin, naloxane+pentazocine, nartograstim, nedaplatin, nilutamide, noscapine, novel crythropoiesis stimulating protein, NSC 631570 octreotide, oprelvekin, osaterone, oxaliplatin, paclitaxel, pamidronic acid, pegaspargase, peginterferon alfa-2b, pentosam polysulfate sodium, pentostatin, picibanil, pirarubicin, rabbit antithymocytepolyclonal antibody, polyethylene glycol interferon alfa-2a, porfimer sodium, raloxifene, raltitrexed, rasburicase, rhenium Re 186 etidronate, RIT retinamide, rituximab, romutide, samarium (153 Sm) lexidronam, sargramostim, sizofiran, sobuzoxane, sonermin, strontium-89 chloride, suramin, tasonermin, tazarotene, teganfur, temoporfin, temozolomide, teniposide, tetrachlorodecaoxide, thalidomide, thymalfasin, thyrotropin alfa, topotecan, toremifene, tosiumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lystate vaccine, valrubicin, verteporfin, vinorelkine, VIRULIZIN, zinostatin stimalamer, or zoledronic acid; abarelix, AE 941 (Actema), ambamustine, antisense oligonucleotide be1-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Mikhaus), leridistim, lintuzumab, CA 125 MAb (Biomira), cancer MAb (Japan Pharmaceutical Development), HER-2 and Fe MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including:

N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

3-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfoncyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluoro-benzylamino)-nicotinamide, 6-fluoro-N-(4-(1-methylethyl)phenyl)-2-((4-pyridinylmethy)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-((4-pyridinylmethyl)amino)-3-pyridinecarboxamide;

N-(3,3-dimethyl-2,3-dihyrdo-1-benzofuran-6-yl)-2-((4-pyridinylmethyl)amino)-3-pyridinecarboxamide;

N-(3-((((2S)-1-methyl-21-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;

N-(4-pentafluoroethyl)-3-(((2S)-2-pyrrolidinylmethyl)oxy)phenyl)-2-((4-pyridinylmethyl)amino)-3-pyridinecarboxamide;

N-(3)-((3-azetidinylmethyl)oxy)-5-(trifluoromethyl)phenyl)-2-((4-pyridinylmethyl)amino)-3-pyridinecarboxamide;

N-(3-(4-piperidinyloxy)-5-(trifluoromethyl)phenyl)-2-((2-(3-pyidinyl)ethyl)amino)-3-pyridinecarboxamide;

N-(4,4-dimethyl-1,2,3,4-tetrahydro-isoquinolin-7-yl)-2-(1H-indazol-6-ylamino)-nicotinamide;

2-(1H-indazol-6-ylamino)-N-[3-(1-methylpyrrolidin-2-ylmethoxy)-5-trifluoromethyl-phenyl]-nicotinamide;

N-[1-(2-dimethylamino-acetyl)-3,3-dimethyl-2,3-dihydro-1H-indol-6-yl]-2-(1H-indazol-6-ylamino)-nicotinamide:

2-(1H-indazol-6-ylamino)-N-[3-(pyrrolidin-2-ylmethoxy)-5-trifluoromethyl-phenyl]-nicotinamide;

N-(1-acetyl-3,3-dimethyl-2,3-dihydro-1H-indol-6-yl)-2-(1H-indazol-6-ylamino)-nicotinamide;

N-(4,4-dimethyl-1-oxo-1,2,3,4-tetrahydro-isoquinolin-7-yl)-2-(1H-indazol-6-ylamino)-nicotinamide;

N-[4-tert-butyl)-3-(3-piperidylpropyl)phenyl][2-(1H-indazol-6-ylamino)(3-pyridyl)]carboxamide;

N-[5-tert-butyl)isoxazol-3-yl][2-(1H-indazol-6-ylamino)(3-pyridyl)]carboxamide; and N-[4-tert-butyl)phenyl][2-(1H-indazol-6-ylamino)(3-pyridyl]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990, 141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkin's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereof), EGFR inhibitory agents (e.g., antibodies or antigen binding regions that specifically bind thereto) such as VECTIBIX™ (pamitumumab), IRESSA™ (gefitinib), TARCEVA™ (erlotinib), anti-Ang1 and anti-Ang2 agents (e.g., antibodies or antigen binding regions specifically binding thereof or to their receptors, e.g., Tie2/Tek, AMG386), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically bind to PDGF-BB ligands, and PDGFR kinase inhibitor agents (e.g., antibodies or antigen binding regions that specifically bind thereto).

Additional anti-angiogenic/anti-tumor agents include SD-7784 (Pfizer, USA); cilengitide (Merck KGaA, Germany, EPO 770622); pegaptanib octasodium, (Gilead Sciences, USA); Alphastatin, (BiaActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, USA); (Amgen, USA); CEP-7055, (Cephalon, USA); anti-Vn Mab, (Crucell, Netherlands) DAC:antiangiogenic, (ConjuChem, Canada): Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praccis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HTP-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system intraocular, 2-methoxyestradiol, (EntreMed, USA); anginex, (Maastricht University, Netherlands, and Minnesota University, USA); ABT 510, (Abbot, USA); AAL 993, (Novartis, Switzerland); VEGI, (Proteom Tech, USA); tumor neocrosis factor-alpha inhibitors, (National Institute of Aging, USA); SU 11248, (Pfizer, USA and SUGEN, USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sima, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co. USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, matrixmetalloprotease inhibitors (MMP), COX-2 inhibitors including celecoxib, NSAID's, or $\alpha_v\beta_3$ inhibitors.

The compound to be administered in combination with AMG 706 hydrate can be formulated separately from the AMG 706 hydrate or co-formulated with the AMG 706 hydrate in a composition of the invention. Where AMG 706 hydrate is co-formulated with a second drug, the second drug can be formulated in immediate-release, rapid-onset, sustained-release or dual-release form.

Processes for preparing AMG 706 are set forth in U.S. Pat. Nos. 6,995,162 and 6,878,714, incorporated herein by reference.

EXAMPLES

The following examples illustrate aspects of the present invention but are not to be construed as limitations.

Example 1

AMG 706 anhydrous diphosphate (~100 mg) salt was added to 2 mL of water and placed on a rotator stirrer. Multiple runs were performed each at different temperatures between about room temperature to about 40° C. Solid was isolated at various time points by vacuum filtering the supernatant and the material was air-dried overnight.

TABLE 1

| Solubility: | | | |
|---|---|---|---|
| time (hr) | Temp (C.) | Solubility (mg/mL) | pH |
| 0.5 | RT | 22 | 2.6 |
| 1.0 | RT | 21 | 2.7 |
| 3.0 | RT | 21 | 2.7 |
| 6.0 | RT | 21 | 2.6 |
| 24.0 | RT | 21 | 2.9 |
| 6.0 | 40 | 20 | 2.6 |
| 24.0 | 40 | 26 | 3.0 |

The monophosphate dihydrate salt was isolated and characterized by various analytical tools for its physico-chemical properties. Interconversion kinetics of anhydrous diphosphate to monophosphate dihydrate was studied under various conditions. The properties of the monophosphate dihydrate material is presented in Table 2 and FIGS. 1 and 3.

TABLE 2

| Stoichiometry and Elemental Analysis | | |
|---|---|---|
| Tests | Theory % | Found % |
| Elemental Analysis | | |
| C | 52.07 | 52.06 |
| H | 5.96 | 5.80 |
| N | 13.80 | 13.85 |
| O | 22.07 | Not tested |
| P | 6.10 | Not tested |
| Free Base Content (HPLC) | 73.59 | 74.1 |
| Stoichiometric ratio between $H_3PO_4$ and Free Base (IC Analysis) | 1:1 | 0.9:1 |

Example 2

AMG 706 diphosphate salt (30 g) was added into 200 mL of boiling de-ionized (DI) water in a 300 mL beaker with magnetic stirring. The solution was protected form light and cooled to ambient temperature (about 20° C.) overnight. The needle-shaped fine crystals were collected using vacuum filtration. The filtration cake was rinsed using about 20 mL of DI water to wash off the yellow color and further dried on the filtration funnel with vacuum for about 7 hours. The collection of the dried solid from the filtration cake yielded AMG 706 monophosphate dihydrate. DSC, and TGA were performed on the material.

Example 3

The thermogravimetric analysis (TGA, Hi-Res TGA 2950, TA Instruments) of AMG 706 monophosphate dihydrate was determined via a thermal analyzer (Universal Analysis 2000, TA Instruments). Heating rates of 10° C./min were employed over a temperature range of 30° C. to 220° C. FIG. 3 shows TGA thermogram for the crystals of Example 1. A first significant thermal event was observed at about 125° C. weight loss, with an onset of about 199° C. is indicative of degradation.

Example 4

The thermal properties of AMG 706 monophosphate dihydrate was characterized with differential scanning calorimetry (DSC, Q100, TA Instrument). Samples were weighed into a non-hermetically crippled aluminum pans and heated at 10° C./min. FIG. 1 shows DSC thermogram for the crystals of Example 1. A first significant thermal event was observed at about 100° C. representing an endothermic event indicative of loss of bound water. As was shown by the presence of a endothermic peak, the resulting material melted and decomposed at about 215° C. FIG. 2 shows a DSC thermogram for the standard crystalline AMG 706.

The foregoing is merely illustrative of the invention and is not intended to limit the invention to the disclosed compounds. Variations and changes which are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions. Although this invention has been described with respect to specific embodiments, the details of these embodiments are not to be construed as limitations.

All mentioned references, patents, applications and publications, are hereby incorporated by reference in their entirety, as if here written.

What is claimed is:

1. A hydrate phosphate salt form of N-(2,3-dihydro-3,3-dimethyl-1H-indol-6-yl)-2-[(4-pyridinylmethyl)amino]-3-pyridinecarboxamide, wherein said hydrate phosphate salt form of N-(2,3-dihydro-3,3-dimethyl-1H-indol-6-yl)-2-[(4-pyridinylmethyl)amino]-3-pyridinecarboxamide exhibits an endothermic peak onset at about 125° C. by differential scanning calorimetry.

2. The hydrate phosphate salt form of N-(2,3-dihydro-3,3-dimethyl-1H-indol-6-yl)-2-[(4-pyridinylmethyl)amino]-3-pyridinecarboxamide of claim 1 wherein the hydrate is the dihydrate.

3. A dihydrate phosphate salt form of N-(2,3-dihydro-3,3-dimethyl-1H-indol-6-yl)-2-[(4-pyridinylmethyl)amino]-3-pyridinecarboxamide.

4. A hydrate phosphate salt form of N-(2,3-dihydro-3,3-dimethyl-1H-indol-6-yl)-2-[(4-pyridinylmethy)amino]-3-pyridinecarboxamide comprising about 5.7% to about 8.5% water.

5. The hydrate of claim 3 comprising about 7.1% water.

6. A hydrate phosphate salt form of N-(2,3-dihydro-3,3-dimethyl-1H-indol-6-yl)-2-[(4-pyridinylmethy)amino]-3-pyridinecarboxamide comprising a stoichiometry of about 1.6—about 2.4 moles water to N-(2,3-dihydro-3,3-dimethyl-1H-indol-6-yl)-2-[(4-pyridinylmethy)aminol]-3-pyridinecarboxamide.

7. The hydrate of claim 6 possessing a stoichiometry of about 2 moles water to N-(2,3-dihydro-3,3-dimethyl-1H-indol-6-yl)-2-[(4-pyridinylmethyl)amino]-3-pyridinecarboxamide.

8. A hydrate phosphate salt form of N-(2,3-dihydro-3,3-dimethyl-1H-indol-6-yl)-2-[(4-pyridinylmethyl)amino]-3-pyridinecarboxamide comprising about 74% of N-(2,3-dihydro-3,3-dimethyl-1H-indol-6-yl)-2-[(4-pyridinylmethyl)amino]-3-pyridinecarboxamide.

9. A hydrate phosphate salt form of N-(2,3-dihydro-3,3-dimethyl-1H-indol-6-yl)-2-[(4-pyridinylmethy)amino]-3-pyridinecarboxamide comprising a stoichiometry of about 0.9—about 1.1 moles phosphate to N-(2,3-dihydro-3,3-dimethyl-1H-indol-6-yl)-2-[(4-pyridinylmethy)amino]-3-pyridinecarboxamide.

* * * * *